United States Patent
Poras et al.

(10) Patent No.: US 10,399,936 B2
(45) Date of Patent: Sep. 3, 2019

(54) INDUSTRIAL PROCESS FOR THE PREPARATION OF (5S, 10S)-10-BENZYL-16-METHYL-11, 14, 18-TRIOXO-15, 17, 19-TRIOXA-2,7,8-TRITHIA-12-AZAHENICOSAN-5-AMINIUM(E)-3-CARBOXYACRYLATE SALT

(71) Applicant: PHARMALEADS, Paris (FR)

(72) Inventors: Herve Poras, Villepreux (FR); Loic Lefebvre, Canteleu (FR); Xinjun Zhao, Dalian (CN); Luca Gamberoni, Comerio Va (IT); Sabrina De Rosa, Cervignano del Friuli Ud (IT); Rosario Velardi, Udine Ud (IT)

(73) Assignee: PHARMALEADS, Paris (FR)

( * ) Notice: Subject to any disclaimer, the term of this patent is extended or adjusted under 35 U.S.C. 154(b) by 0 days.

(21) Appl. No.: 15/767,966

(22) PCT Filed: Oct. 14, 2016

(86) PCT No.: PCT/EP2016/074709
§ 371 (c)(1),
(2) Date: Apr. 12, 2018

(87) PCT Pub. No.: WO2017/064250
PCT Pub. Date: Apr. 20, 2017

(65) Prior Publication Data
US 2018/0305308 A1    Oct. 25, 2018

(30) Foreign Application Priority Data
Oct. 14, 2015    (EP) .................................... 15306626

(51) Int. Cl.
| C07C 323/25 | (2006.01) |
| C07C 319/02 | (2006.01) |
| C07C 319/22 | (2006.01) |
| C07C 319/24 | (2006.01) |
| C07C 319/28 | (2006.01) |
| C07C 327/32 | (2006.01) |
| B01J 19/18  | (2006.01) |
| C07D 215/26 | (2006.01) |
| C07C 323/40 | (2006.01) |

(52) U.S. Cl.
CPC ......... *C07C 323/25* (2013.01); *B01J 19/1862* (2013.01); *C07C 319/02* (2013.01); *C07C 319/22* (2013.01); *C07C 319/24* (2013.01); *C07C 319/28* (2013.01); *C07C 327/32* (2013.01); *C07D 215/26* (2013.01); *B01J 2219/0004* (2013.01); *B01J 2219/00029* (2013.01); *C07B 2200/07* (2013.01); *C07C 323/40* (2013.01)

(58) Field of Classification Search
None
See application file for complete search history.

(56) References Cited

FOREIGN PATENT DOCUMENTS

WO    2007/048787 A1    5/2007

OTHER PUBLICATIONS

Campbell, I.G.M. et al., The Chrysanthemumcarboxylic Acids, J. Sci. Food Agric., 1952, 3:189-192.
Fournie-Zaluski, M-C et al., "Mixed Inhibitor-Prodrug" as a New Approach toward Systemically Active Inhibitors of Enkephalin-Degrading Enzymes, J. Med. Chem, 1992, 35:2473-2481.
Kadoudin, B. et al., Resolution of Enantiomers of Novel C(subscript)2-Symetric Aminobisphosphinic Acids via Diastereomeric Salt Formation with Quinine, Chirality, 2015, 27(1):71-74.
Poras, H. et al., New Orally Active Dual Enkephalinase Inhibitors (DENKIs) for Central and Peripheral Pain Treatment, J. Med. Chem., 2014, 57:5748-5763.
PCT International Application No. PCT/EP2016/074709, International Search Report dated Nov. 11, 2016.

*Primary Examiner* — Ana Z Muresan
(74) *Attorney, Agent, or Firm* — Pillsbury Winthrop Shaw Pittmann LLP

(57) ABSTRACT

The present invention relates to an industrial process for the preparation of (5S,10S)-10-benzyl-16-methyl-11,14,18-trioxo-15,17,19-trioxa-2,7,8-trithia-12-azahenicosan-5-aminium (E)-3-carboxyacrylate salt of following formula (I): wherein X is fumarate. This process comprises the following successive key steps: a kinetic resolution, formation of disulfide compound, peptide coupling, and anion exchange reaction to obtain the desired product of formula (I).

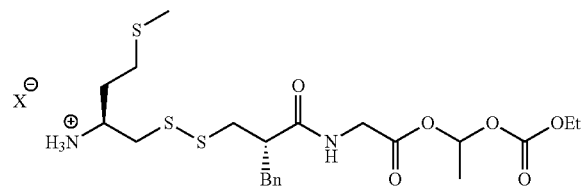

19 Claims, 2 Drawing Sheets

INDUSTRIAL PROCESS FOR THE PREPARATION OF (5S, 10S)-10-BENZYL-16-METHYL-11, 14, 18-TRIOXO-15, 17, 19-TRIOXA-2,7,8-TRITHIA-12-AZAHENICOSAN-5-AMINIUM(E)-3-CARBOXYACRYLATE SALT

RELATED APPLICATIONS

This application is the National Phase of International Application No. PCT/EP2016/074709, filed on Oct. 14, 2016 which designated the U.S. and that International Application was published under PCT Article 21(2) in English, and claims priority to European Patent Application No. 15306626.1, filed on Oct. 14, 2015. The entire content of the foregoing applications are expressly incorporated herein by reference in their entirety, including all text, tables and drawings.

TECHNICAL FIELD

The present invention relates to a new industrial process for the preparation of (5S,10S)-10-benzyl-16-methyl-11,14,18-trioxo-15,17,19-trioxa-2,7,8-trithia-12-azahenicosan-5-aminium (E)-3-carboxyacrylate salt, by combining 3-(acetylthio)-2-benzylpropanoic acid moiety and (S)-tert-butyl 1-mercapto-4-(methylthio)butan-2-ylcarbamate and 2-(1-(ethoxycarbonyloxy)ethoxy)-2-oxoethanaminium chloride.

BACKGROUND OF THE INVENTION (5S, 10S)-10-benzyl-16-methyl-11,14,18-trioxo-15,17,19-trioxa-2,7,8-trithia-12-azahenicosan-5-aminium (E)-3-carboxyacrylate salt, referred herein as "Compound (I)" of following formula:

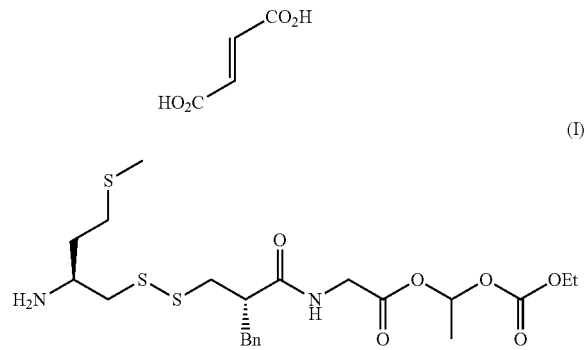

is a pro-drug of the asymmetric disulfide which is composed of the selective neutral aminopeptidase (APN) inhibitor, ((S)-1-mercapto-4-(methylthio)butan-2-aminium), and of the selective neprilysin (NEP) inhibitor, ((S)-2-(2-benzyl-3-mercaptopropanamido)acetic acid). Compound (I) has been proven to be an efficient painkiller, as described by Poras et al. in J Med Chem, 2014, 57, 5748-5763.

Compound (I) and its use as painkiller were first disclosed in patent application WO2007/048787. The process exemplified in WO 2007/048787 allows the preparation of compound (I), in 4 steps from 3-(acetylthio)-2-benzylpropanoic acid (A), (S)-tert-butyl 1-mercapto-4-(methylthio)butan-2-ylcarbamate (B) and 2-(1-(ethoxycarbonyloxy)ethoxy)-2-oxoethanaminium chloride (C). Technical synthetic specifications, particularly enzymatic resolution, numbers of equivalents, solvents and/or purification techniques involved in this process, do not allow it to be efficiently and easily converted into an industrial scale.

A permanent aim in organic synthesis is to create synthesis processes that can be transposed into industrial conditions. In order to meet requirements for industrial processes, different parameters of the synthesis are to be optimized. Firstly, solvents must be as little volatile as possible, in order to be easily recoverable.

The temperatures involved preferably remain in an easily accessible range, and easy to proceed purification should be privileged. Finally, reactions mixtures and isolated products are preferably thermally stable.

Current Good Manufacturing Practice (c-GMP) has been defined for preparation of drug products for administration to humans or animals. GMP regulations require a quality approach to manufacturing, enabling companies to minimize or eliminate instances of contamination, mix-ups, and errors.

To the applicant knowledge, no industrially applicable process to synthesize the compound (I) has been described so far. Therefore, a need remains for a process for preparing compound (I) that can be adapted easily and efficiently to industrial scale, in particular a process wherein toxic solvents such as chlorinated solvents, enzyme resolution, and column chromatography are not used.

SUMMARY OF THE INVENTION

The present invention relates to an industrial process for the preparation of (5S,10S)-10-benzyl-16-methyl-11,14,18-trioxo-15,17,19-trioxa-2,7,8-trithia-12-azahenicosan-5-aminium (E)-3-carboxyacrylate salt of following formula (I):

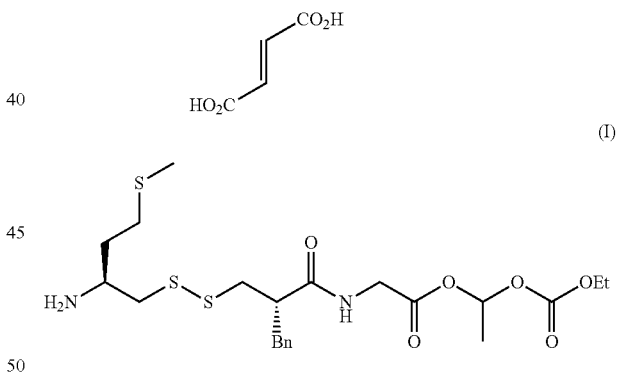

This process comprises the following successive synthetic steps performed in degassed organic polar or apolar, protic or aprotic solvents:

1. Preparing compound E of following formula with an enantiomeric excess higher than 95%

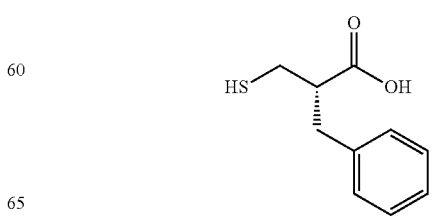

By

1a) Reacting A of following formula

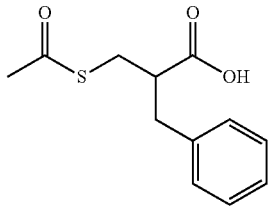

With 0.5-0.6 molar equivalents of quinine in organic polar and aprotic solvents;

1b) Crystallizing the resulting quinine salt at temperature ranging from 10° C. to 20° C., in same organic solvent than the one used in step 1a, wherein crystallization is initiated by adding few crystals of the desired enantiomer salt to initiate the crystallization, then;

1c) Recrystallizing the salt obtained after step 1b at the same temperature range and same solvent than the one used in step 1b;

1d) Recovering of compound E by:

1d.1) recovering compound (D) of following formula

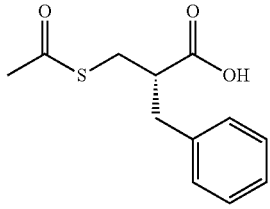 [SMILES: CC(=O)SC[C@@H](Cc1ccccc1)C(=O)O]

1d.2) deprotecting thiolacetate in polar and protic solvent such as MeOH;

1e) Recovering of quinine;

2. Preparing compound F of following formula

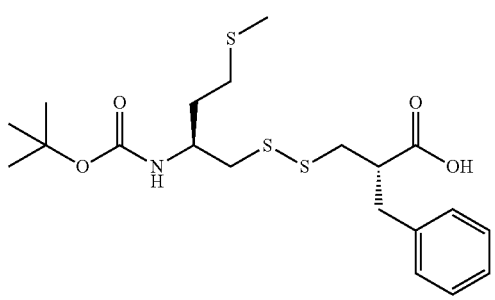 [SMILES: CSCC[C@@H](CSSC[C@@H](Cc1ccccc1)C(=O)O)NC(=O)OC(C)(C)C]

by

2a) Reacting first 1.1 molar equivalents of said compound E with 1 molar equivalent of chlorocarbonyl sulfenyl chloride, in polar and aprotic solvent, then;

2b) Reacting the intermediate obtained after step 2a with 0.9 molar equivalents of compound B of following formula

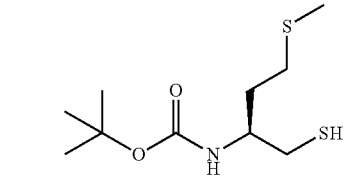

In solution with 1 molar equivalent of Et₃N in same solvent than the one used in step 2a;

3. Preparing compound G of following formula

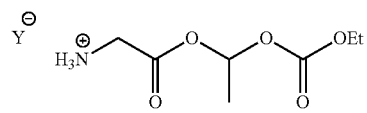

By

Reacting said compound F with amino-ester C of following formula, wherein Y⁻ is an anion:

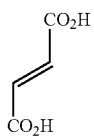

In polar solvent;

4. Then, recovering salt (I) of followed formula

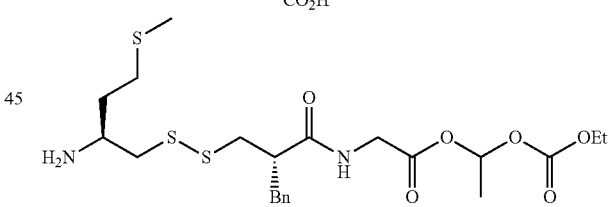

by 4a) adding 5 molar equivalent of formic acid on said compound G;

4b) exchanging the formiate by a fumarate using a continuous flow technology.

DETAILED DESCRIPTION OF THE INVENTION

In the present, the following abbreviation mean:
AcOEt: ethyl acetate
Bn: Benzyl
Boc: tert-Butoxycarbonyl
DCM: dichloromethane
DME: dimethoxyethane
DMF: dimethyl formamide
ee: enantiomeric excess EtOH: ethanol
HBTU: O-Benzotriazol-1-yl-N,N,N',N'-tetramethyluronium hexafluorophosphate
HPLC: High Performance Liquid Chromatography
IPC: In Process Control
MeOH: methanol
THF: tetrahydrofuran One of the object of the present invention relates to a general method for the preparation of (5S,10S)-10-benzyl-16-methyl-11,14,18-trioxo-15,17,19-trioxa-2,7,8-trithia-12-azahenicosan-5-aminium (E)-3-carboxyacrylate salt of following formula (I)

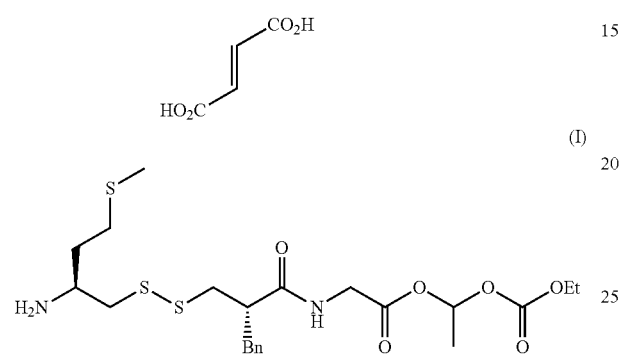

Comprising the following steps:

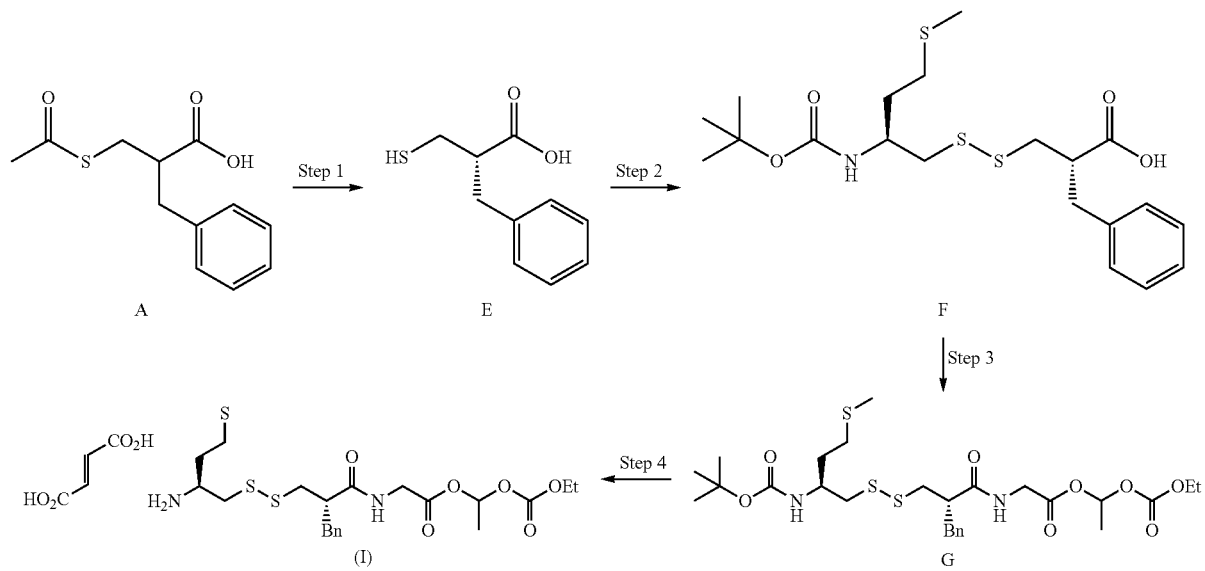

Step (1): Synthesis of compound E, by a kinetic resolution of (A) with quinine to give (S)-3-(acetylthio)-2-benzyl-propanoic acid (D), followed by an alkaline hydrolysis of the acetyl moiety of (D) giving (S)-2-benzyl-3-mercaptopropanoic acid (E), and recovering quinine;

Step (2): Synthesis of the asymmetric disulfide (S)-2-benzyl-3-(((S)-2-(tert-butoxycarbonylamino)-4-(methylthio)butyl)disulfanyl)propanoic acid (F), composed of (B) and (E) by activation with chlorosulfonylchloride in polar aprotic solvent;

Step (3): Synthesis of (6S,11S)-1-(ethoxycarbonyloxy)ethyl 11-benzyl-2,2-dimethyl-6-(2-(methylthio)ethyl)-4,12-dioxo-3-oxa-8,9-dithia-5,13-diazapentadecan-15-oate (G) by a peptide coupling between compound (F) obtained after step (2) and glycine ester cascade (C);

Step (4): Recovering salt (I) by deprotection of Boc protecting group, followed by an anion continuous flow exchange reaction.

Step (1)

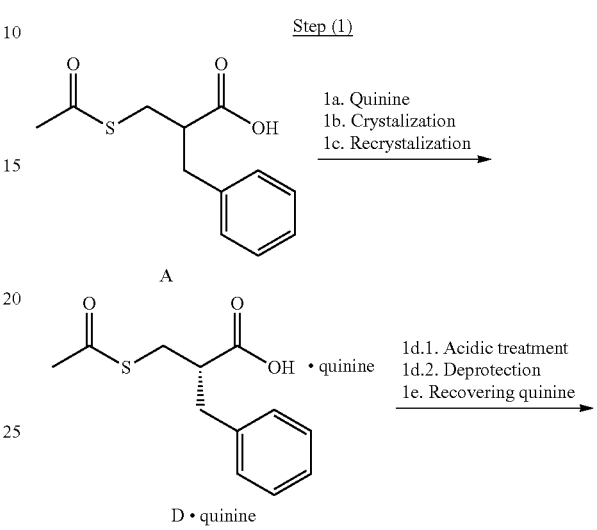

-continued

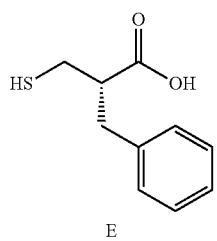

E

The quinine recovered in step 1e can be used again in step 1a.

In WO2007/048787, (S)-3-(acetylthio)-2-benzylpropanoic acid (D) was obtained via enzymatic resolution of the racemic compound with alpha-chymotrypsin. The resolution could also be performed with trypsin. While these allowed producing compound (I) with good chiral purity, the process was difficult to perform at industrial scale plant.

In the invention, step 1a involves a kinetic resolution of commercially available racemic 2-acetylthio-3-phenylpropionic acid (A) using a chemical resolving agent, preferably performed with quinine of following formula:

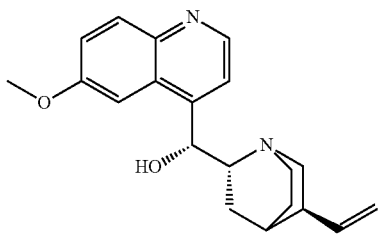 [SMILES: C=C[C@@H]1CN2CCC1C[C@@H]2[C@H](O)c1ccnc2ccc(OC)cc12]

in a polar and aprotic solvent.

In a preferred embodiment the kinetic resolution is performed in AcOEt.

In step 1b, the resulting quinine salt is crystallized at temperature ranging from 10° C. to 20° C., in same organic solvent than the one used in step 1a, wherein crystallization is initiated by adding few crystals of the desired enantiomer with quinine to initiate the crystallization. It was demonstrated that the use of a seed was important to secure robustness of the initial crystallization, at temperature ranging from 10° C. to 20° C. In present description, "seed" means few crystals of the desired enantiomer of compound (D) with quinine to initiate the crystallization.

Advantageously, crystallization in step 1b comprises the following successive steps:
1b.1) dissolution of quinine salt at solubilizing temperature, then;
1b.2) cooling the mixture obtained in step 1b.1 until temperature ranging from 10° C. to 20° C.;
1b.3) isolating quinine salt obtained after step 1b.2 by filtration.

In a preferred embodiment, the crystallization in step 1b is realized by heating a quinine-salt mixture until complete dissolution of said quinine salt in suspension in polar and aprotic solvent. In step 1b.1, the quinine salt is advantageously heated until complete dissolution. In particular, in step 1b.1 the solubilizing temperature ranges from 38° C. to 50° C.

After step 1b.1, the mixture is then cooled until temperature ranging from 10° C. to 20° C. Advantageously in step 1b.2 the cooling is performed at a rate of 3-10° C./h.

Once the temperature is reached, the mixture is advantageously maintained at the temperature for a period of 10-30 hours, in particular 10-20 hours.

The enantiomeric enriched crystal quinine salt is obtained after a filtration, and then put into a recrystallization step 1c. Step 1c comprises recrystallization of the salt obtained after step 1b at the same temperature range and same solvent than the one used in step 1b. In industrial point of view, it is indeed more efficient and economical to use the same solvent.

In a preferred embodiment, the recrystallization in step 1c comprises the following successive steps:
1c.1) dissolution of quinine salt at solubilizing temperature, then;
1c.2) cooling the mixture obtained in step 1c.1 until temperature ranging from 10° C. to 20° C.;
1c.3) isolating quinine salt obtained after step 1c.2 by filtration;
1c.4) step 1c.1 to 1c.3 is optionally repeated.

In particular, in step 1c.1, the mixture is heated until complete dissolution of said quinine salt. Advantageously, in step 1c.1 the solubilizing temperature ranges from 45° C. to 65° C.

In an illustrative embodiment, the kinetic resolution with quinine give 90% of enantiomeric excess after a single crystallization, and 95.5% of enantiomeric excess could be obtained after recrystallization of the quinine salt. The mole ratio of chemical resolving agent and racemic compound (A) has to be 0.5-0.6/1, in particular 0.55/1.

All these key parameters allowed obtaining compound (D) in a consistent manner with chiral purity above 95%, purity above 98% and an average molar yield of 38% starting from racemic compound (A), compared to 27% yield starting from racemic compound (A) in case of enzymatic resolution (WO2007/048787).

In particular, the steps (1a) to (1c) typically comprise the following successive steps:
Addition of quinine to a solution rac-3-(acetylthio)-2-benzylpropanoic acid in AcOEt;
Complete dissolution by heating at temperature ranging from 38° C. to 50° C.;
Cooling temperature from 5° C. and then seeding, then;
Cooling in 5 hours (rate of 3-10° C.) to temperature ranging from 10° C. to 20° C. then keeping the reaction mixture at the same temperature range for 16 hours;
Isolation of (S)-3-(acetylthio)-2-benzylpropanoic acid.quinine salt by filtration;
Suspension of the said salt in AcOEt;
Complete dissolution by heating until solubilizing temperature (range from 45° C. to 60° C.) of the said salt is reached;
Cooling in 9 hours to temperature ranging from 10° C. to 20° C.;
Isolation of (S)-3-(acetylthio)-2-benzylpropanoic acid.quinine salt by filtration.

The recovering of compound E comprises the following successive steps:
1d.1) recovering compound (D) of following formula

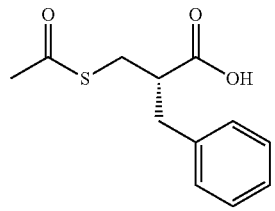 [SMILES: CC(=O)SC[C@@H](Cc1ccccc1)C(=O)O]

1d.2) deprotecting thiolacetate in polar and protic solvent such as MeOH

In a preferred embodiment, step 1d.1 further comprises the following successive steps:
1d.1.1) suspension of quinine salt obtained in step 1c.3 or 1c.4 in acidified water until pH ranges from 1 to 3, in particular with a mix of HCl/water, then;

1d.1.2) extraction of compound (D) of following formula

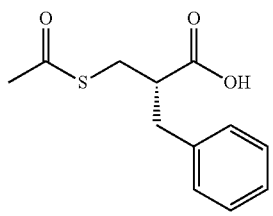 [SMILES: CC(=O)SC[C@@H](Cc1ccccc1)C(=O)O]

an aprotic and apolar solvent, in particular with AcOEt, then;
1d.1.3) concentration in vacuum to obtain an oil.

Advantageously, step 1d.2 comprises the following successive steps:
1d.2.1) Alkaline hydrolysis in polar and protic solvent, then;
1d.2.2) Acidic treatment, then;
1d.2.3) Extraction of compound (E) with organic solvent, in particular with AcOEt.

Preferably, the hydrolysis in step 1d.2.1 is performed with 0.5M aqueous solution of NaOH in polar and protic solvent, in particular methanol. In a preferred embodiment, the reaction is performed at temperature ranging from 15° C. to 28° C. during 20-40 min, in particular 20 min. Advantageously, the acidic treatment in step 1d.2.2 is realized as follows:
the reactional mixture is acidified until pH is lower than 7, in particular with a mixture of 6N HCl in water, then;
adding zinc dust (0.15-0.20 g, in particular 0.18 g for 1 g Compound (D)), and then;
stirring the mixture at temperature ranging from 2° C. to 8° C., in particular at 5° C., till all the disulfide by-product is converted to the thiol product.

Since both ethyl acetate and water do not interfere in the subsequent step, the final solution is not dried and the product (E) is kept dissolved at concentration of 40% of its initial volume in order to have an easy to handle product.

As expected, the said product (E) is sensitive to air because of formation of disulfide by-product. Thus, all the liquids used were degassed under inert gas atmosphere. The compound (E), if properly stored, is stable for at least 3 days at room temperature. Due to difficulty in obtaining and storing an analytical standard of the product, the quantitative analysis of the concentrate solution is performed by NMR, whereas the purity is checked by HPLC.

Finally, the recovering of quinine is performed in step 1e.

In a preferred embodiment, step 1e comprises the following successive steps:
1e.1) Combining the aqueous phases obtained in step 1d.2.1 and in step 1d.2.2, then;
1e.2) Adding 20% by weight of aqueous solution of NaOH in water to adjust the pH to 12, then;
1e.3) Extracting the resulting mixture obtained in step 1e.2 with AcOEt, then;
1e.4) Concentrating under vacuum the resulting organic layer obtained in step 1e.3, then;
1e.5) Adding petroleum ether at temperature ranging from 10° C. to 20° C., then;
1e.6) Filtrating the resulting solid obtained at the end of step 1e.5 and recovering quinine.

The possibility to re-use quinine is a further advantage of the process of the invention, leading to a more economical process.

In an illustrative embodiment, step 1 is realized starting from 195 kg of racemic 2-acetylthio-3-phenylpropionic acid (A), the compound (D) could be obtained in a 68% yield using quinine as resolving agent. 154.6 kg of S-2-acetylthio-3-phenylpropionic acid quinine salt were obtained (chiral purity 97.5%). The potential recycling of quinine base has been demonstrated at lab scale (80% yield).

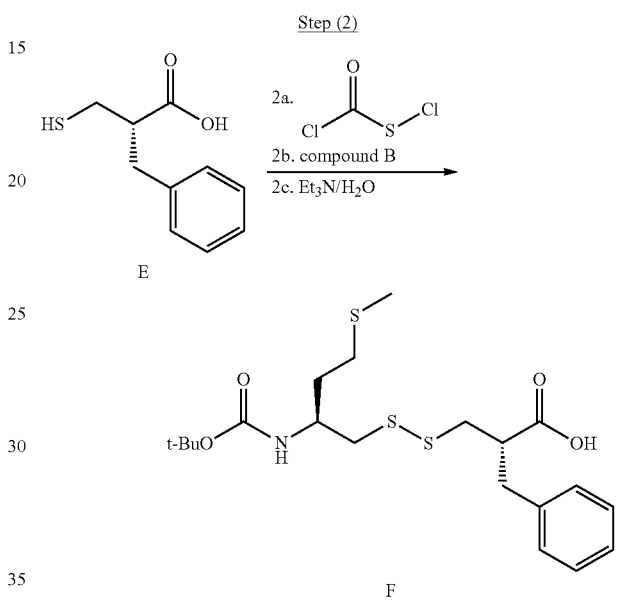

In WO2007/048787 application, (E) reacted with (B) which has been activated with chlorosulfonylchloride, in MeOH/THF, to provide (S)-2-benzyl-3-(((S)-2-(tert-butoxycarbonylamino)-4-(methylthio)butyl)disulfanyl)propanoic acid (F).

In the present invention, the preparation of compound F of following formula, comprises the following successive steps

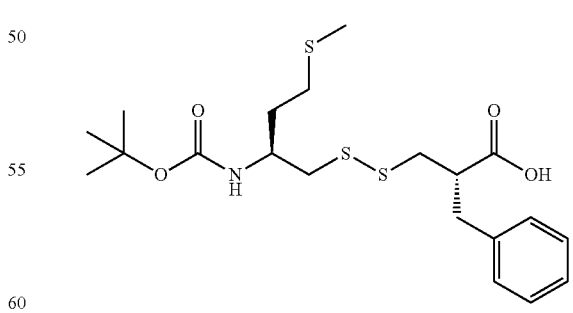

2a) Reacting first 1.1 molar equivalents of said compound E with 1 molar equivalent of chlorocarbonyl sulfenyl chloride, in polar and aprotic degassed solvent, then;
2b) Reacting the intermediate obtained after step 2a with 0.9 molar equivalents of compound B of following formula

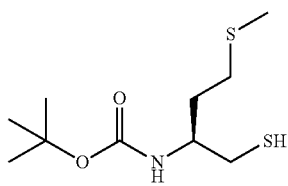

In solution with 1 molar equivalent of Et₃N in same degassed solvent than the one used in step 2a;

In particular, in step 2a, the polar and aprotic solvent is AcOEt.

In a preferred embodiment, chlorocarbonyl sulfenyl chloride useful in step 2a, is activated in THF, in particular at concentration of 0.2M-0.4M, preferably at concentration of 0.33M, before its addition, in step 2a, on a solution of compound (E) at 0.1M-0.2M, preferably at 0.15M in polar and aprotic solvent, preferably the said solvent is AcOEt.

Before the said addition, the reaction mixture of chlorocarbonyl sulfenyl chloride is cooled at temperature ranging from −2° C. to 5° C., preferably at 0° C. under inert atmosphere for 10-20 min, in particular 15 min. Advantageously, the mixture of activated chlorocarbonyl sulfenyl chloride is added all at once, and then the resulting solution is returned to temperature ranging from 15° C. to 25° C., preferably 22° C., and is further agitated during 20-40 min, preferably 30 min.

In a preferred embodiment, in step 2b, the resulting mixture obtained after step 2a is added dropwise to a solution of compound B at concentration of 0.6M-1.0M, preferably at 0.9M, with 1 molar equivalent of Et₃N to chlorocarbonyl sulfenyl chloride, in polar and aprotic solvent, in particular in THF. The resulting solution is then agitated during 1-2 h, preferably 1 h, at a temperature ranging from 15° C. to 25° C., preferably 22° C.

The specific quantity of molar equivalents of compound (B) in step 2b allows avoiding impurity of its symmetric disulfide. This is important since the said impurity is very difficult to remove from the desired product.

At the end of step 2b, the solvent is advantageously evaporated under reduce pressure and the resulting crude product is taken up in AcOEt.

Advantageously, after step 2b the following successive steps are performed:

2b.1) adding water comprising 10% weight of citric acid to the reaction mixture obtained after step 2b, until pH<7, then;

2b.2) extracting compound F with AcOEt.

In preferred embodiment, after step 2b.2, the compound (F) is precipitated in Hexane and AcOEt and the said compound (F) can be recrystallized in a mixture of Hexane/AcOEt, in 5.5/1-7.5/1 in a volume proportion, preferably 6.5/1 in a volume proportion.

All the solvents were degassed under inert atmosphere, to avoid oxidation of sulfide.

In the present invention, the synthesis of compound B, useful for the synthesis of compound F, is changed from the WO application, and the process comprises the following synthetic steps:

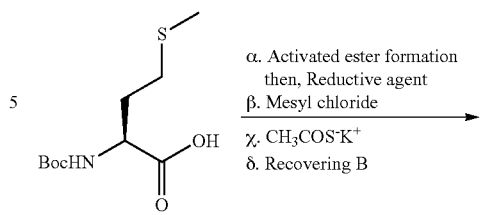

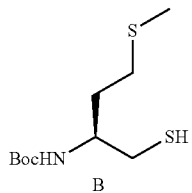

The compound (B) was obtained with a 60% molar yield by a process of 5 steps, starting from commercially available Boc-L-Methionine (synthetic origin) as described in the patent application WO2007/048787.

In first step α, the carboxylic acid moiety of Boc-L-methionine reacts with i-butyl chloroformate in presence of N-Methylmorpholine in DME according to the procedure of J. Med. Chem., 35, 1992, 2473. The resulting activated ester is not isolated and reacts consequently with a selective reductive agent of esters. In particular, the reductive reagent is for example NaBH₄. In step β, the Boc-amino alcohol obtained after step α, is then protected by hydroxyl protecting group, in particular mesyl group by using the corresponding mesyl chloride.

In step χ, a nucleophilic substitution of hydroxyl protecting group is then realized in presence of potassium thioacetate.

Finally, in step δ, compound (B) is recovered after a saponification type reaction. Advantageously the saponification is performed by using a solution of 1M NaOH in MeOH.

In a preferred embodiment in step δ, the volume of methanol used for the hydrolysis has been reduced by 30%, compared to quantity used in WO2007/048787 proceeding.

The molar equivalents of NaOH, in step δ, have been advantageously reduced from 3 to 2; and this change allows reducing the amount of acid needed for the neutralization with an overall gain in the process productivity.

It was found in a preferred embodiment in step δ, that a fast addition of the base reduces the amount of disulfide formed, provided that the temperature remains below 10° C. advantageously to a range of 0° C.-10° C.

In particular, following the base addition and after stirring 1-2 h the resulting basic mixture, the temperature of the reaction, in step δ, has also been increased from 18° C.-25° C. to 28° C.-35° C., in this way the reaction time has been reduced to 0.5 h, with respect to 2 h of the initial procedure described in WO2007/048787.

In this case, the work-up has been advantageously changed: the concentration of methanol is performed at pH about 7, since it was observed that the Boc protecting group is labile in both basic and acidic conditions. Moreover, in order to reduce the overall time of the process, only one extraction in organic solvent is advantageously performed, and no aqueous washes of the organic phase are made, compared to the initial procedure in WO2007/048787.

In particular, the final solution is not concentrated to oily residue but to a molar concentration of about 35% (as determined by quantitative NMR), since the solvent of the subsequent step has been changed.

This process has been scaled up to 50 kg scale. As expected the free thiol is highly sensitive to oxygen, giving rise to the corresponding disulfide, so in order to avoid the formation of said disulfide side product, all the solvents and reagents were degassed with several vacuum/inert gas cycles.

Step (3):

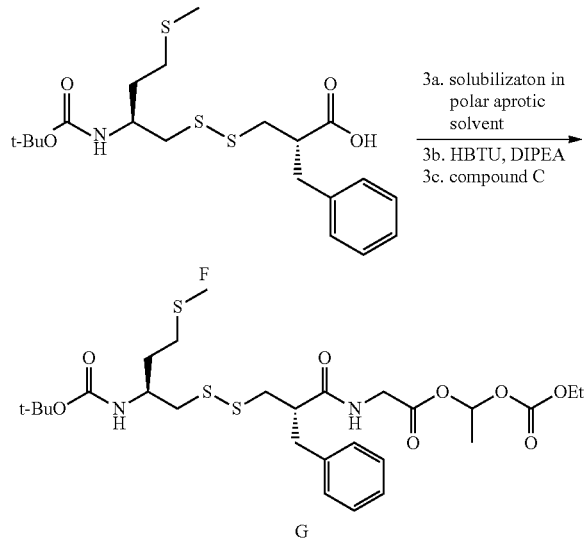

In the present invention, the compound G of following formula

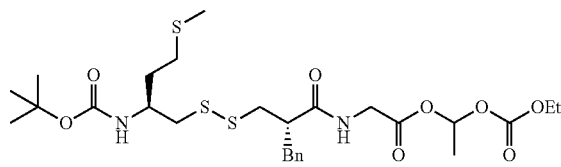 [SMILES: CCOC(=O)OC(C)OC(=O)CNC(=O)[C@@H](CSSC[C@H](CCSC)NC(=O)OC(C)(C)C)Cc1ccccc1]

is synthesized, in a polar solvent, by reacting the said compound F with amino-ester C of following formula, wherein Y⁻ is an anion:

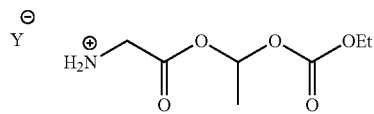

In a preferred embodiment, the step 3 comprises the following successive steps:

3a) solubilizing compound F in polar and aprotic solvent, then;

3b) to the reaction mixture obtained after step 3a, adding 1.2 molar equivalents of O-Benzotriazol-1-yl-N,N,N',N'-tetramethyluronium hexafluorophosphate and diisopropyl-ethyl-amine, then;

3c) to the reaction mixture obtained after step 3b, adding 1.3 molar equivalent of aminoester C.

In step 3a, the compound (F) is advantageously put in organic solvent at a concentration of 0.05M-0.3M, preferably at 0.1M. In a preferred embodiment, compound (F) is solubilized in DMF.

In a preferred embodiment, the mixture is agitated during 5-10 min at temperature ranging from 2 to 10° C., in order to avoid the formation of by-product.

After step 3c and before step 4 compound G is preferably obtained by following successive steps:

3c.1) recovering organic layer containing compound G;

3c.2) precipitate compound G present in organic layer of step 3c.1 by adding a mixture of petroleum ether (n-Hexane)/AcOEt in 8/1-6/1 volume proportion, preferably 7/1 volume proportion.

In a preferred embodiment, step 3c.1 comprises the following successive steps:

3c.1.1) adding water to the resulting mixture obtained in step 3c, then;

3c.1.2) without concentrating the reaction solvent, extracting the product obtained after step 3c.1.1 with polar aprotic solvent, preferably AcOEt.

In particular in step 3c.1.2, the product is purified by precipitation with a mixture of petroleum ether (n-Hexane) and AcOEt at temperature ranging from 20° C. to 25° C. without column chromatography. Compound G is stable at temperature ranging from 18° C. to 25° C., and was obtained with 87% molar yield up to 43.7 kg scale.

In the present invention, the synthesis of compound C, useful in step 3c, is changed from the WO application, and the process comprises the following steps:

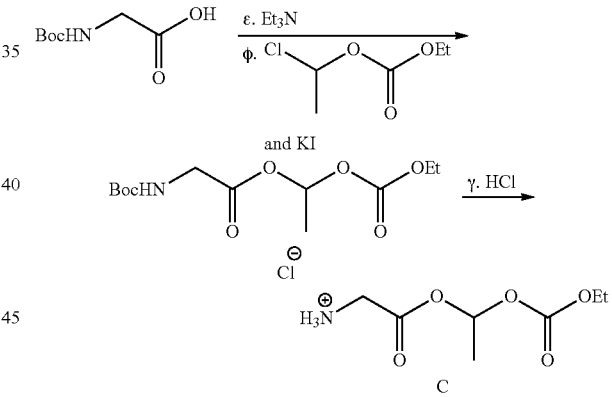

In a preferred embodiment, compound C is prepared by a process comprising following successive synthetic steps:

ε) reacting 1.1 molar equivalents of Boc-glycine with 1.2 molar equivalents of Et₃N in polar and aprotic solvent, then;

φ) reacting product obtained in step ε with 1 molar equivalent of ethyl-1-chloroethylcarbonate, and 0.2 molar equivalents of potassium iodide in same solvent as in step ε, then;

γ) reacting product obtained in step φ with 2 molar equivalents of HCl gas in AcOEt at temperature ranging from 5° C. to 10° C., and recovering C.

In a preferred embodiment in step ε, the stoichiometry has been changed and the amount of Boc-glycine has been increased to 1.1 molar equivalents, with respect to 0.95 molar equivalents in WO2007/048787, and that of Et₃N to 1.2 molar equivalents from 1 molar equivalent. The polar and aprotic solvent used in step ε, is preferably a mixture of AcOEt/DMF in 10/1 weight/weight proportion. The introduction of DMF as co-solvent is performed to increase the polarity and the boiling point of the reaction mixture. The temperature of step ε and φ is advantageously the reflux temperature.

At the end of step φ only one acidic washing with 10% weight of citric acid in water, is preferably made to remove the excess of base, compared to WO2007/048787 proceeding, whereas the second basic washing with 10% weight of NaHCO₃ in water, allow for complete removal of the excess of Boc-Glycine.

Due to the instability of the product obtained after step φ, on silica gel, the process control is performed by NMR instead of by TLC. The product is a yellow oil and stable at temperature ranging from 18° C. to 25° C.

In particular in step φ, potassium iodide has been used instead of the corresponding sodium salt, since it has a higher solubility in AcOEt and is more easily available on the market. Due to this property the molar amount of potassium iodide catalyst has been advantageously lowered to 0.2 molar equivalents (instead of 0.3 molar equivalents used in WO2007/048787). An amount of potassium iodide lower than 0.2 molar equivalents decreases the reaction rate.

In step γ, for the preparation of glycine «cascade» ethyl ester salt (C), the presence of water in the starting solution gives a loss of yield, due to the solubility of the product. For this reason, an IPC has been preferably introduced to measure the amount of residual water in the organic solution, before the Boc-amino group deprotection in step γ (the water content in AcOEt should be not higher than 0.1% by weight).

Preferably for the step γ, the introduction of AcOEt as solvent instead of DCM with respect with WO2007/048787 proceeding enables to decrease the effect of residual water in the starting solution.

In particular the acid used in step γ, is a dry HCl gas, and in this way, it is possible to use only 2 molar equivalents of the said acid. Probably due to the higher solubility of dry HCl gas in AcOEt, it was found in particular in step γ that, with 2 molar equivalents of acid, the conversion is higher at temperature ranging from 5° C. to 10° C. than at temperature ranging 20° C. to 25° C.

The order of addition was advantageously inverted, namely a solution of the protected amino acid obtained after step γ, was added to a cold solution of the said acid. Another advantage of the inverse addition is that the product begins to precipitate really early, thus preserving the quality of the isolated product (C).

In a preferred embodiment, it was found that addition of the protected amino compound obtained after step β, on acidic solution in 2-4 h, preferably in 3 h, allowed to a more complete reaction.

In this case, due to nature of the product, NMR was chosen as analytical technique for the evaluation of the conversion. If the amount of impurity determined by NMR is at least 0.5%, the purification of the product by washing with isopropanol has to be done. The product is a white to light yellow solid. It is stable at room temperature but is sensitive to moisture.

In an illustrative embodiment the synthesis of compound (C) has been scaled-up at 30 kg scale without any problem in 69% yield starting from commercially available Boc-Glycine.

Preferably, following the Barcelo et al. procedure (Synthesis, 1986, 627), in the case of the synthesis of ethyl 1-chloroethylcarbonate useful in step φ. AcOEt was used as the solvent instead of DCM.

In a preferred embodiment, the use of pyridine is preferred instead of Et₃N to decrease the amount of impurities during the synthesis of ethyl 1-chloroethylcarbonate.

In particular, the stoichiometry of the reaction has been changed: the amount of ethanol and pyridine has been increased to 1.05 and 1.1 molar equivalents, respectively. This modification allowed a higher conversion of the starting material, without affecting the quality of the desired ethyl 1-chloroethylcarbonate at the end of the work-up.

The temperature of the reaction mixture during the addition of pyridine has been advantageously increased, keeping it below 10° C. This allows an easier temperature control on large scale production: therefore, the reaction temperature has been kept in a range from 2° C. to 8° C. throughout the reaction time. Due to the increase in molar amount of ethanol and pyridine added, the reaction time has been shortened to around 1 hour reaction time.

Preferably, the work-up has been changed, in particular the filtration of the salts has been avoided and only two washes (one acidic and one basic) of the organic phase are made.

Due to the instability of the ethyl 1-chloroethylcarbonate and to the absence of chromophoric groups, NMR has been chosen as analytical technique. The product is a light yellow oil and stable at temperature ranging from 18° C. to 28° C., preferably at 22° C.

Step (4)

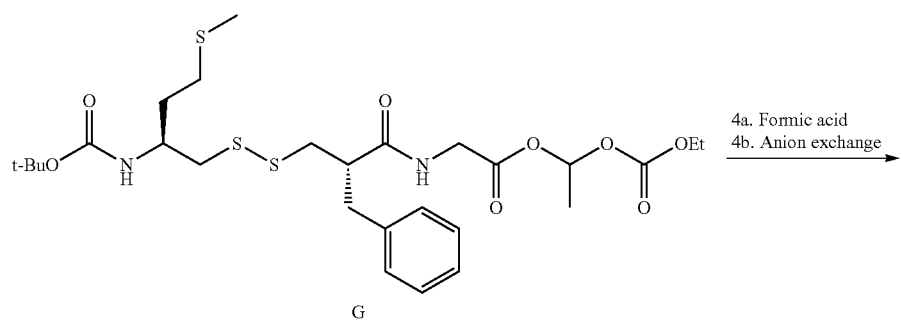

4a. Formic acid
4b. Anion exchange

G

-continued

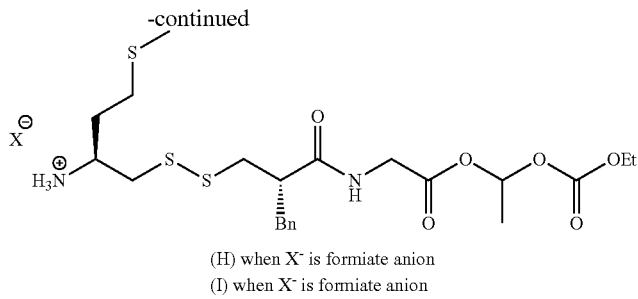

(H) when X⁻ is formiate anion
(I) when X⁻ is formiate anion

In the present invention, the recovering of salt (I) of followed formula

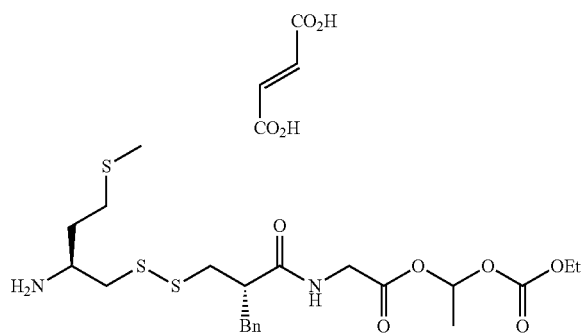

Comprises the following successive steps:
4a) adding 5 molar equivalents of formic acid on said compound G
4b) exchanging the formiate by a fumarate using a continuous flow technology.

The deprotection of the Boc-amino group of (G) is performed in acidic condition, using formic acid, to give (5S,10S)-10-benzyl-16-methyl-11,14,18-trioxo-15,17,19-trioxa-2,7,8-trithia-12-azahenicosan-5-aminium formiate salt (H).

In preferred embodiment in step 4a, after adding formic acid, the process further comprises the following successive steps:
4a.1) co-evaporating product obtained after adding formic acid with toluene giving compound (H) and organic layer with toluene, then;
4a.2) adding AcOEt to the compound (H) obtained after step 4a.1, and washing the resulting mixture with brine at a temperature ranging from 0° C. to 10° C.

In step 4a.1, the compound (H) obtained is in particular co-evaporated several times with toluene until the excess of formic acid is removed.

In a preferred embodiment in step 4b, anion exchange is performed by flow continuous process comprising the following successive steps:
4b.1) at temperature ranging from 0° C. to 10° C., maintaining a solution of 3.3% by weight of compound (H) in AcOEt at pH ranging from 8 to 9, preferably by adding a solution of 2% NaOH by weight in water to the said solution of compound (H), then;
4b.2) adding a solution 5% fumaric acid by weight in EtOH to the mixture obtained after step 4b.1 to isolate crystallized compound (I) using flow continuous process.

The flow continuous process is an automatic procedure wherein reagents are added in continuous in reactor instead of charged in only one time. This method presents several advantages like the stoichiometry control by relative flow, the mixing is fast and complete and the temperature is uniform. In the present process, this allows unstable intermediate to exist in low quantity and in transitional manner.

At the end of step 4a.2, a solution of 3.3% by weight of compound (H) is prepared in AcOEt, and then used in anion exchange reaction in step 4b with fumaric acid.

The anion exchange reaction in step 4b represents the key phase of the process, because amino free base, advantageously obtained after step 4b.1, once generated from the corresponding formate salt (H), has to be preferably converted as soon as possible to the fumarate salt (I) which in turn has to be quickly crystallized, in order to avoid secondary reactions.

It was observed during preliminary c-GMP batch synthesis that performing these operations batch wise, the by-products formation increased with the scale of the preparation. As a consequence, the set-up of these operations in continuous mode permits resolving the problem of scaling up the process.

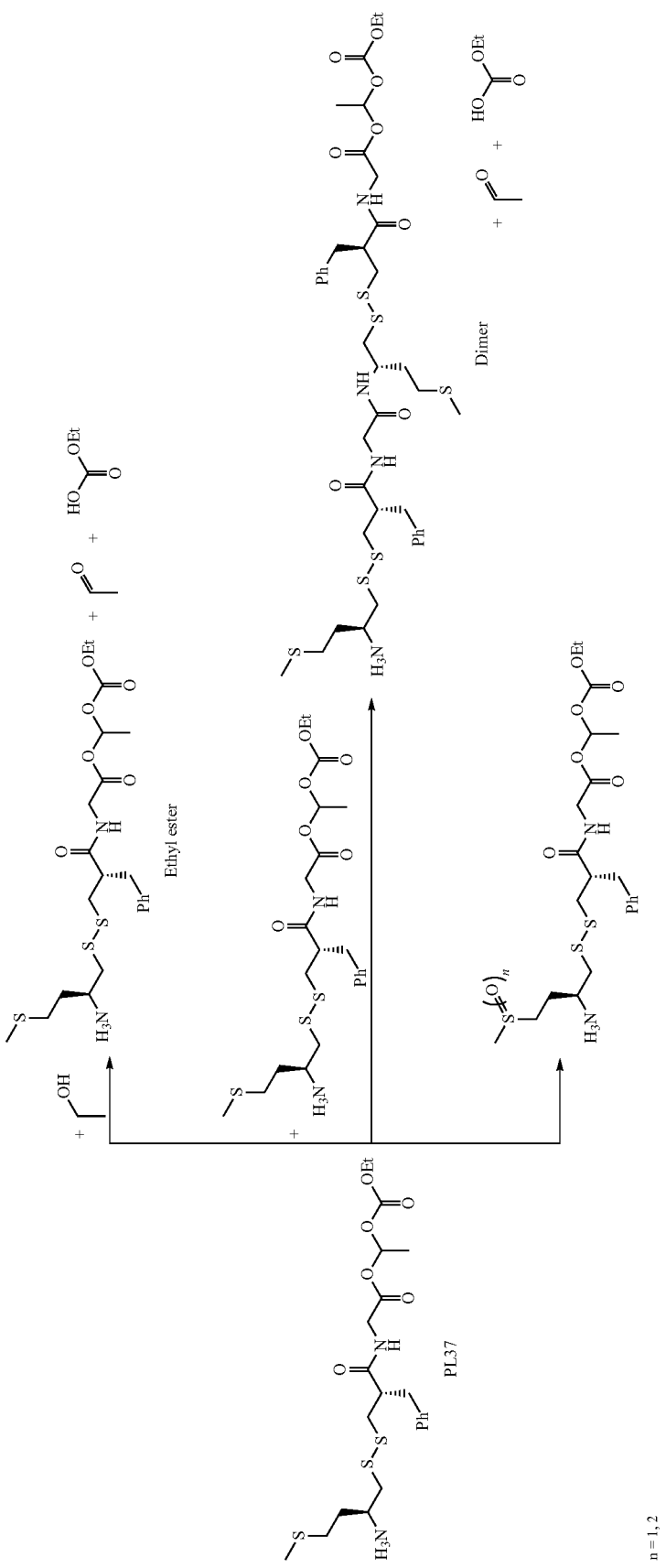
Scheme 4: Possible pathway for decomposition of free amino base of compound (I).

The critical phase in formation of compound (I) is step 4b wherein the compound (H) is treated in basic conditions. The said step 4c give the free amino base of compound (I), which is unstable. The free amino base can evolve to ethyl ester, dimer and oxidized sulfide compound. The continuous flow process permits to avoid these impurities formations.

For the realization of step 4b, the solution of 3.3% by weight of compound (H) in AcOEt was introduced via 1. Consecutively, the solution of 2% NaOH by weight in water was added via 2.

Step 4b.1: the mixture reacted continuously at 5° C. and at pH ranging from 8-9, allowing a conversion of the formate salt (H) into the free base compound (I).

In section 3, we obtained a biphasic mixture, which was then extracted continuously, at 5° C. in 4. Water phase was stored in container in 5, and the organic phase obtained in 6, was engaged in step 4b.2. A solution of 5% fumaric acid by weight in EtOH was introduced via 7, to the step 4b.2. The mixture in step 4b.2 reacted continuously at 5° C. A solution of compound (I) was obtained in 8. A continuous distillation of solvent was then performed in 9. Distilled solvent was stored in container in 10, and the compound (I) was obtained in 11.

Figure 1:
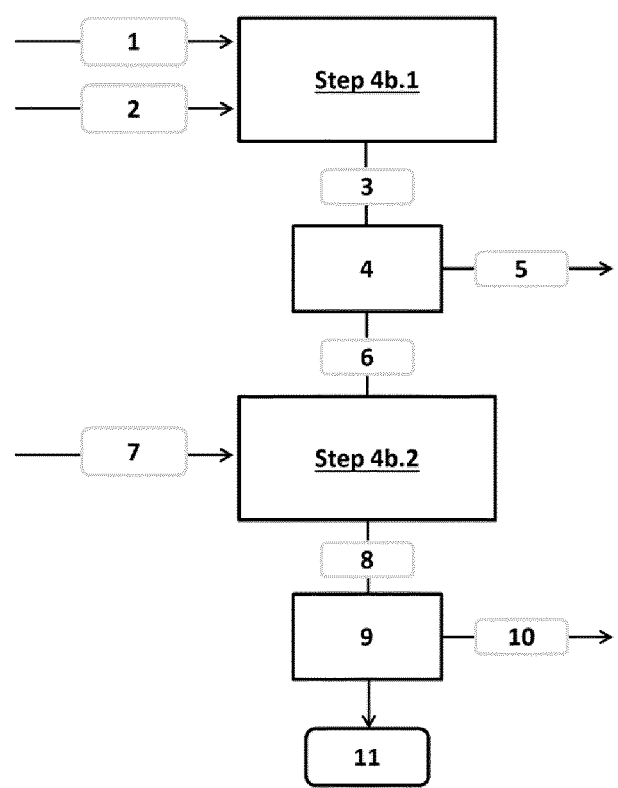
FIG. 1 describes the block diagram of step 4b exposing the continuous flow process.
Figure 2:
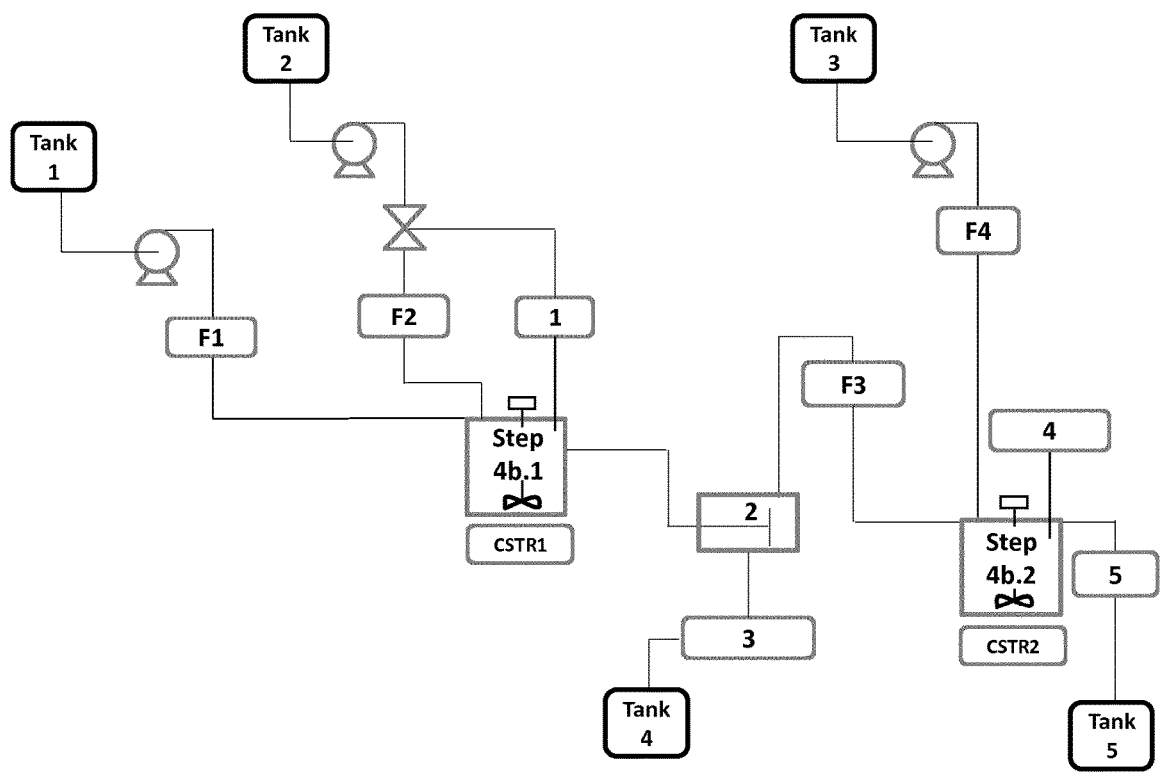

FIG. 2 describes the continuous apparatus for the preparation of compound (I).

For the realization of step 4b at an industrial scale, the continuous apparatus consisting of a mixer-settler and a Continuous Stirred Tank Reactor (CSTR2) was assembled. The mixer-settler was formed by a Continuous Stirred Tank Reactor (CSTR1) and a settler 4. CSTR1 was the reactor wherein step 4b.1 was performed. CSTR2 was the reactor wherein step 4b.2 was performed.

Tank 1 was charged with the solution of 3.3% by weight of compound (H) in AcOEt, and the said solution was engaged into CSTR1 reactor with a feed F1 at 1095 g/h. Consequently, Tank 2 was charged with the solution of 2% NaOH by weight in water and the said solution was then engaged in CRST1 reactor with a feed F2 at 348 g/h. The pH was controlled via 1 during all the stirring to maintain it at a range from 8 to 8.5. The biphasic reaction mixture overflew from CSTR1 into the settler where phases were separated. The aqueous phase was stored in Tank 4 with an outflow 3 of 375 g/h. The organic phase containing compound (I) free base was engaged in CSTR2 reactor with a feed F3 at 1068 g/h. Consequently, Tank 3 was charged with the solution of 5% fumaric acid by weight in EtOH and the said solution was then engaged in CRST2 reactor with a feed F4 at 142 g/h.

F4 was regulated in order to have a molar ratio of 0.95 between theoretical amount of compound (I) contained in F3 and fumaric acid. The reaction mixture containing compound (I) solution overflew from CSTR2 into Tank 5 with an outflow 5 of 1201 g/h, wherein the said solution containing compound (I) was collected and stored for the length of experiment.

All the equipment was thermostated at temperature of 5° C.

Concentration of crude compound (I) fumarate solution resulting from the continuous process was completed by batch wise vacuum distillation, and then crystallization was achieved in Diisopropyl Ether. Compound (I) was obtained as a white solid, with an overall molar yield, from compound (F), of 84%.

Isolated compound (I), obtained according to the developed method, was analyzed by HPLC, and compared with the compound (I) sample, obtained according to the previous batch procedure (WO2007/048787).

Content of impurities is significantly lower in the compound (I) sample from continuous process.

In an illustrative embodiment, flow continuous process was performed with 0.15 kg of compound (G) scale size.

EXAMPLES

In the present invention, "room temperature" means a temperature ranging from 18° C. to 28° C., preferably ranging from 20° C. to 25° C.

1—Studies on Quinine Quantity Useful for the Step 1.

Different quinine providers are tested as resolving agent in conditions described above for the kinetic resolution in step 1 (Table 1). The obtained results showed that a slight difference in chiral purity with Vital Health Care sample.

TABLE 1 different quinine providers tested for the kinetic resolution in step 1

| Supplier | Purity | Yield (Oil) | S/R ratio | ee | Yield (S) |
|---|---|---|---|---|---|
| Vital Health Care | 99% | 35% | 97.1:2.9 | 94.2% | 68% |
| Buchler | 99.10% | 35.25% | 96.1:3.9 | 92.2% | 67.75% |

It was hypothesised that both quinine samples had a different assay and therefore a different equivalent of "pure quinine" was used in both trials.

Using Buchler sample, the resolution was tested with three different molar equivalents of quinine (0.5, 0.55 and 0.6) starting from racemic mixture of compound (A), and giving the compound (D) isolated as oil (Table 2).

TABLE 2

Kinetic resolution with different molar equivalents of quinine Buchler provider.

| Equiv. | Purity | Yield (Oil) | S/R (Solid cryst) | S/R (Oil) | ee | Yield (S) |
|---|---|---|---|---|---|---|
| 0.50 | 98.40% | 32.1% | 92.8:7.2 | 98.7:1.3 | 97.4% | 63.4% |
| 0.55 | 99.52% | 33.7% | 90.1:6.8 | 98.7:1.2 | 97.5% | 66.6% |
| 0.60 | 99.10% | 35.25% | 88.9:10.6 | 96.1:3.9 | 92.2% | 67.7% |

These tests showed that an excess of quinine compared to the 0.5 molar equivalents of S-enantiomer led to a loss of chiral purity.

In an opposite trend, lowering equivalent of quinine to 0.5 molar equivalents and using 1 molar equivalent of compound (A) led a decrease in recovering of S enantiomer (63.4% vs 66.6%) without significant chiral purity gain. These results could explain why a better chiral purity could be obtained using 0.6 molar equivalent of quinine of a lower assay (Table 2). Since quinine sample from Buchler was taken from an industrial batch in stock and given its superior quality profile, Buchler was selected as the provider.

In an illustrative embodiment, 0.55 molar equivalents of quinine were preferably retained from laboratory trials as compromise for chiral purity and enantiomer recovery.

The solid quinine salt was tested by thermal stress at 100° C. for 36 hours and it is assumed to be stable at this stage. Despite a change of aspect from white crystalline to semi-melted beige solid, the sample did not displayed visible degradation by HPLC.

In an industrial point of view, the storing of compound (D) is made under its corresponding quinine salt, and the said quinine salt is then engaged in the following step 1d.2 wherein the solvent is switched from ethyl acetate to methanol.

2—Step a: Resolution/Recrystallization

A resolution on 5 kg scale is described on Table 3.

TABLE 3

Materials used for resolution of 5 kg of compound (A) with Quinine

| Material | M.W. | Quantity | Moles | Eq. |
|---|---|---|---|---|
| 2-Acetylthiomethyl-3-phenylpropionic acid | 238.3 | 5000 g | 21 mol | 1 |
| Quinine | 324.4 | 4080 g | 12.6 mol | 0.6 |
| AcOEt | | 170 L | | |
| Conc. HCl aqueous solution | | 2 L | | |
| (S)-2-acetylthiomethyl-3-phenylpropionic acid | 238.3 | 1884 g (75% mol. Yield related to (S) enantiomer, 98.95% chemical purity, 99.5% chiral purity | | |

Maximum volume: 103 L

General Procedure for Industrial Kinetic Resolution:

Different parameters were evaluated and a typical procedure is described below.

Industrial Preferred Procedure for Crystallization:

1) Charging 90 L of AcOEt, 5.0 kg (21 mol) of compound (A) and 4.08 kg (12.6 mol) of quinine in a reactor;
2) Rinse the addition funnel with 10 L of AcOEt to flush the solid detained on the wall of the funnel into the reactor, and stir the mixture at temperature ranging from 10° C. to 15° C. for 20 min;
3) Heating the mixture to 45° C. and stirring the mixture at 45° C. till a clear solution was formed;
4) Cooling down the solution at a speed of 5° C./h to 40° C.;
5) Adding 1 g of seed which have 86% of chiral purity;
6) Cooling down the mixture at a speed of 5° C./h to temperature ranging from 10° C. to 20° C.;
7) Stirring the mixture at temperature ranging from 10° C. to 15° C. for an additional 16 h;
8) Filtering the quinine salt product after crystallization and keeping the filtrate in a container (the room temperature was 11° C. when the mixture was followed out and filtered);
9) Analyzing the filter cake with HPLC to check the chiral purity, preferably 84% of chiral purity is obtained;

Industrial Preferred Procedure for Recrystallization:

10) Charging the wet cake obtained in the operation 9 in another reactor;
11) Adding 70 L of AcOEt;
12) Heating the mixture at 60° C. and under stirring till the entire solid was dissolved;
13) Cooling down the solution at a speed of 5° C./h to room temperature (when the temperature reaches 40° C., the precipitate started to be formed);
14) Stirring the mixture at temperature ranging from 10° C. to 15° C. overnight (16 h);
15) Filtering the recrystallized quinine salt (the room temperature was 11° C. when the mixture was flowed out and filtered) and keeping the filtrate in a container;
16) Analyzing the filter cake with HPLC to check the chiral purity, preferably 95.5% of chiral purity is obtained;

Recovering the AcOEt Solvent Used in Preceding Process (Operations 1 to 16):

17) Charging 30 L of the filtrate obtained in the operation 15 in a reactor;
18) Adding 10 L of 0.5 M aqueous solution of NaOH in water, until pH>10, and stirring the mixture at room temperature for 20 min;
19) Separating the organic phase and storing the aqueous phase in a container;
20) Analyzing the organic phase with HPLC.

If 2-acetylthiomethyl-3-phenylpropionic acid (A) cannot be detected, go to next operation. If it can be detected, wash the organic phase with water till no 2-acetylthiomethyl-3-phenylpropionic acid (A) can be detected in the organic phase;

Recovering Free Compound (D):

21) Transferring the organic phase obtained in operation 19 into a reactor;
22) Adding the wet cake obtained in the operation 15;
23) Adding 10 L of water and 2 L of aqueous solution of HCl 12 N and stirring the mixture at room temperature, for an additional 30 min (pH of the aqueous phase was ~1);
24) Separating the organic phase of product and keeping the aqueous phase in a container;
25) Washing the organic phase with about 5 L of water, and monitoring the washing by HPLC to detect quinine in the organic phase;
26) Concentrating the organic phase at temperature ranging from 40° C. to 45° C. and under vacuum to remove the solvent as complete as possible;
27) Adding 2.5 L of methanol into the residue and concentrating again the mixture at temperature ranging from 40° C. to 45° C. and under vacuum to chase out the remaining solvent of AcOEt;
28) Repeating the operation 27 once to give 2.1 kg of oil product of compound (D);
29) NMR analysis shows a conversion of quinine salt of (D) into free compound (D) of 89.8%. So, 1884 g of compound (D) are obtained with 75.4% yield relative to (S) enantiomer, and 98.9% chemical purity.

2.2 Step b: Recovering of Quinine at the End of Step 1.

Another attractive point of chemical resolution is the recovery of the chiral agent as described below:

1) Charging the remaining filtrate (about 30 L) obtained in the operation of 15 in Step a in a reactor;
2) Adding 10 L of 0.5 M aqueous solution of NaOH in water and stirring the mixture at room temperature, for an additional 20 min (pH of the aqueous phase was about 12);
3) Separating the organic phase and storing the aqueous phase in a container;
4) Washing the organic phase with water and monitoring the washing by HPLC to detect 2-acetylthiomethyl-3-phenylpropionic acid in organic phase;
5) Keeping the organic phase in a container;
6) Charging the filtrate (about 90 L) obtained in the operation 8 in Step a in another reactor
7) Adding 6 L of concentrated aqueous solution of HCl to adjust the pH to 1~2
8) Separating the aqueous phase and store the organic phase in a container for recovering the AcOEt by distillation
9) Combining the aqueous phase obtained in the operations 19 and 24 in Step 1 and the aqueous phase obtained in the operations 3 and 8 in step b;

10) Adding 20% by weight of aqueous solution of NaOH in water to adjust the pH to 12;
11) Adding the AcOEt obtained in the operation 5 and stirring the mixture at room temperature for an additional 20 min;
12) Separating the organic phase and extracting the aqueous phase with 10 L of AcOEt;
13) Combining the organic solutions and concentrating it at temperature ranging from 40° C. to 45° C. and under vacuum to a volume of about 3.0 L;
14) Under vigorously stirring, adding 10 L of petroleum ether at temperature ranging from 10° C. to 20° C.;
15) Stirring the mixture at temperature ranging from 10° C. to 20° C. for an additional 1 h;
16) Filtering the mixture to isolate the solid quinine product;
17) Drying the filter cake at temperature ranging from 50° C. to 55° C. and under vacuum to give 1832 g of white solid product of quinine (80% of recovery).

Using similar procedure, batch such as 150 kg of quinine salt was manufactured.

2.3 Determination of the Ee Value of Compound (D)
Procedure:
1) Mixing L-Ala-OMe.HCl with 1.0 molar equivalent of compound (D) in DCM, then;
2) Stirring at temperature ranging from 10° C. to 20° C. till a solution is formed, then;
3) Adding 1.5 molar equivalents of EDCl and 2 molar equivalents of $Et_3N$ at room temperature, and stirring for an additional 1-2 min, then;
4) Removing the solvent in vacuum, then;
5) Adding AcOEt to dissolve the residue, then;
6) Washing consecutively the solution with 10% in weight of citric acid in water, then with sodium bicarbonate aqueous solution, then with water and then with brine, then;
7) Removing AcOEt and recovering a solid product.
8) Dissolving the said product obtained in operation 7 in $CDCl_3$ for 1H NMR analysis.

Methods for Calculation of the Enantiomeric Excess:
1) Integration of the peak at 6.0 ppm—Integration of the peak at 5.85 ppm (based on the amide proton), or;
2) Integration of the peak at 1.34 ppm—Integration of the peak at 1.04 ppm (based on the methyl proton in the alanine part).

Using protocol described in FIG. 2, a continuous technology scale is described on Table 4.

TABLE 4

Materials used for continuous process.

| Reagents | M.W. | g | mol | d | mL | Molar ratio |
|---|---|---|---|---|---|---|
| Compound (G) | 618.83 | 150.00 | 0.242 | 1.000 | | 1.00 |
| Formic acid | 46.03 | 565 | 12.28 | 1.220 | 463 | 50.65 |
| Toluene (1° charge) | 92.14 | 275 | 2.98 | 0.870 | 316 | 12.30 |
| Toluene (2° charge) | 92.14 | 275 | 2.98 | 0.870 | 316 | 12.30 |
| Theoretical products | | | | | | |
| Compound (H) | 564.74 | 136.89 | 0.242 | | | 1.00 |
| Isobutene | 56.11 | 13.60 | 0.242 | | | 1.00 |
| $CO_2$ | 44.01 | 10.67 | 0.242 | | | 1.00 |

1) Charging 1 L round-bottomed flask with 0.565 kg of formic acid;
2) Maintaining the temperature at 25° C.;
3) Purge a 1 L round-bottomed flask with $N_2$;
4) Charging the 1 L round-bottomed flask with 0.15 kg of compound (G), and maintaining the temperature at 25° C.;
5) Heating the unit 1 L round-bottomed flask to 30° C.;
6) Reacting in the unit 1 L round-bottomed flask via deprotection, for an additional 5 h;
7) Final temperature of the batch is 30° C.;
8) QC-Test the material in the unit 1 L round-bottomed flask is performed in 30 min, and the specification obtained shows: (G)<2%.

If the specification is not met, the test is continued for 1 h more and repeated.
9) Distilling the batch in the unit 1 L round-bottomed flask.
10) The bottom pressure is 80 mm-Hg and the maximum temperature is 40° C.
11) Distilling about 65% of the initial mass;
12) -Charging a 1 L round-bottomed flask with 0.275 kg of toluene.
13) Distill the batch in the unit 1 L round-bottomed flask;
14) The bottom pressure is 65 mm-Hg, and the maximum temperature is 40° C.
15) Distill about 63% of the initial mass;
16) Charging a 1 L round-bottomed flask with 0.275 kg of toluene;
17) Distilling the batch in unit 1 L round-bottomed flask;
18) The bottom pressure is 50 mm-Hg, and the maximum temperature is 40° C.
19) Distilling about 60% of the initial mass;
20) Transferring contents of the unit 1 L round-bottomed flask to a 5 L round-bottomed flask;
21) Transferring 100% of vessel contents;
22) Cooling a unit 5 L round-bottomed flask to temperature ranging from 5° C.;
23) Charging the 5 L round-bottomed flask with 1.99 kg of AcOEt;
24) Maintaining the temperature at a range from 0° C. to 10° C.;
25) Charging the 5 L round-bottomed flask with 1.09 kg of 7.2% weight NaCl solution;
26) Maintaining the temperature at a range from 5° C.;
27) Extracting in the unit 5 L round-bottomed flask over 10 min;
28) The lower layer stream, named water phase from washing, is sent to waste.
29) Charging a 5 L round-bottomed flask with 1.974 kg of AcOEt;
30) Maintaining the temperature at a range from 5° C.;
31) Transferring 100% of vessel contents of the unit 5 L round-bottomed flask to Tank 1;
32) Charging a 1 L flask with 0.56 kg of ethanol;
33) Maintaining the temperature at 25° C.;
34) Charging 1 L flask with 0.0295 kg of (2E)-but-2-enedioic acid;
35) Maintaining the temperature at 25° C.;
36) Transferring 100% of vessel contents of the unit 1 L flask to Tank 3;
37) Continuously reacting the mixture from unit Tank 1 in unit CSTR 1 via reaction neutralization.
38) The mixture feed rate is 1.097 kg/h.
39) The stream is named PL37 formate in AcOEt to continuous section.
40) The final temperature is 5° C.
41) The product stream, named biphasic mixture from neutralization, is sent to settler.
42) Continuously add a solution of 2% NaOH by weight in water from Tank 2 at a rate of 0.348 kg/h and the feed is named 2% NaOH to continuous section;

43) Extracting continuously the mixture from CSTR 1 in the unit Settler;
44) The top layer, named PL37 organic phase from neutralization, is sent to CSTR 2.
45) The bottom layer is sent to waste.
46) Continuously reacting the mixture from settler in unit CSTR 2 via reaction salification with a solution 5% fumaric acid by weight in EtOH.
47) The final temperature is ranging from 5° C.
48) The product stream is sent to Tank 5.
49) Continuously adding the material from tank 3 at a rate of 0.142 kg/h, and the feed is named fumaric acid solution to continuous salification;
50) In order to reach the steady state, the continuous apparatus was operated for 20 min, before starting to collect the compound (I) solution in Tank 5. The amounts of each solution used for reaching the steady state are in table below.

TABLE 5

Amount of solution used to performed continuous formation of compound (I) in Tank 1 to 3.

| Solution | Amount (g) |
| --- | --- |
| F1: solution of 3.3% by weight in compound (H) in AcOEt in Tank 1 | 362 |
| F2: solution of 2% NaOH by weight in water in Tank 2 | 120 |
| F4: solution 5% fumaric acid by weight in EtOH | 48 |

Then, the continuous apparatus was operated for 3.45 h. The input and output streams are outlined in table below.

TABLE 6

Input/Output stream in continuous formation of compound (I) in Tank 1 to 5.

| | Amount (g) | Flow rate (g/h) |
| --- | --- | --- |
| Input Stream | | |
| F1: solution of 3.3% by weight in compound (H) in AcOEt in Tank 1 | 3778 | 1095 |
| F2: solution of 2% NaOH by weight in water in Tank 2 | 1201 | 348 |
| F4: solution 5% fumaric acid by weight in EtOH | 492 | 142 |
| Output Stream | | |
| Compound (I) in solution in Tank 3 | 4142 | 1201 |
| Water phase from neutralization to waste in Tank 4 | 1294 | 375 |

51) Distilling continuously the mixture from unit Tank 5 in unit thin film evaporator. The jacket temperature is 40° C. The residual pressure is 50 mm-Hg. The overhead temperature condenser is −5° C.
52) Distillate stream is sent to waste, and bottom stream, is sent to a 3 L round-bottomed flask.

TABLE 7

Input/Output stream in continuous formation of Compound (I) in Tank 5 to 7.

| | Amount (g) | Flow rate (g/h) |
| --- | --- | --- |
| Input Stream | | |
| Solution of Compound (I) in Tank 5 | 4142 | 1593 |
| Output Stream | | |
| Concentrated solution of Compound (I) in Tank 6 | 500 | 192 |
| Distilled solvents in Tank 7 | 3642 | 1401 |

53) Distill the batch in unit 3 L round-bottomed flask. The overhead is sent to waste. The bottom pressure is 100 mm-Hg, and the maximum temperature is 30° C.
54) Cooling the unit 3 L round-bottomed flask to temperature ranging from 20° C.
55) Charge the 3 L round-bottomed flask with 1.56 kg of diisopropyl ether,
56) The charge time is 70 min.
57) The seed is charged to crystallization
58) Maintaining the temperature ranging from 20° C.
59) Cooling unit 3 L round-bottomed flask to a range from 5° C.
60) Crystallizing the batch in the unit 3 L round-bottomed flask, during 3 h.
61) Filtering the batch from the unit 3 L round-bottomed flask in filter.
62) The transfer time of the slurry is 1 h, and the mother liquor is sent to waste.
63) Washing the cake in unit filter 2 times, in particular for each washing, using 0.10 kg of diisopropyl ether.
64) Transferring 100% of vessel contents of the unit filter to dryer.
65) Drying the batch in unit dryer for an additional time of 16 h, at temperature ranging from 25° C., and the drying pressure is 50 mm-Hg.
66) Transferring contents of the unit dryer to storage.
67) The transfer stream is named dried PL37 fumarate, which is obtained in 118 g, and with overall yield of 84% starting from compound (G).

The invention claimed is:
1. An industrial process for the preparation of (5S,10S)-10-benzyl-16-methyl-11,14,18-trioxo-15,17,19-trioxa-2,7,8-trithia-12-azahenicosan-5-aminium (E)-3-carboxyacrylate salt of following formula (I):

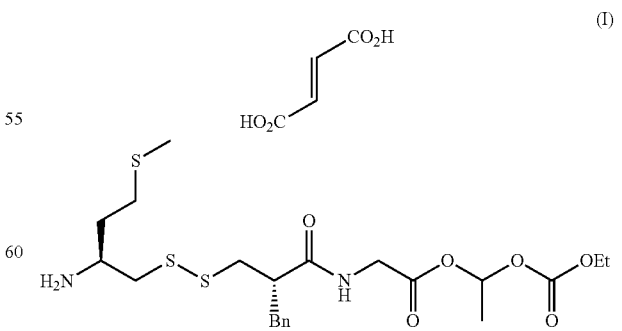

comprising the following successive synthetic steps performed in degassed organic polar or apolar, protic or aprotic solvents:

(1) preparing compound E of following formula with an enantiomeric excess higher than 95%

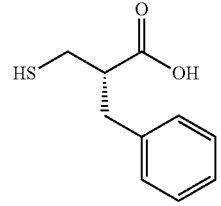
E by
1a) reacting A of following formula

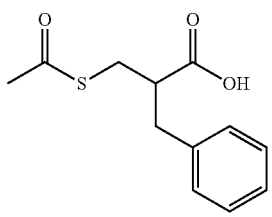
A with 0.5-0.6 molar equivalents of quinine in organic polar and aprotic solvents;

1b) crystallizing the resulting quinine salt at temperature ranging from 10° C. to 20° C., in same organic solvent than the one used in step 1a, wherein crystallization is initiated by adding few crystals of the desired enantiomer salt to initiate the crystallization, then;

1c) recrystallizing the salt obtained after step 1b at the same temperature range and same solvent than the one used in step 1b;

1d) Recovering of compound E by:
  1d.1) recovering compound (D) of following formula

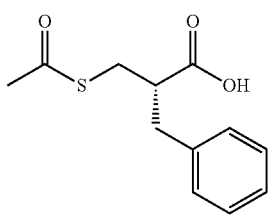
D 1d.2) deprotecting thiolacetate in polar and protic solvent such as MeOH;
1e) recovering of quinine;

(2) preparing compound F of following formula

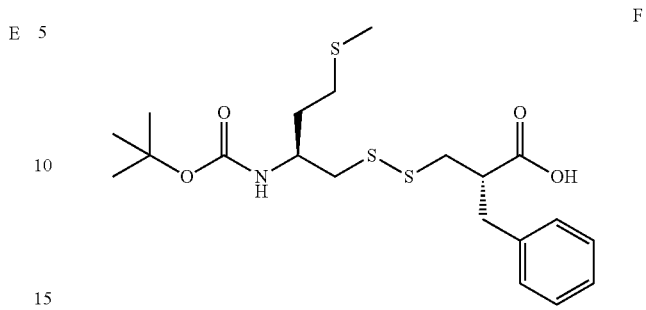
F

By
2a) reacting first 1.1 molar equivalents of said compound E with 1 molar equivalent of chlorocarbonyl sulfenyl chloride, in polar and aprotic solvent, then;

2b) reacting the intermediate obtained after step 2a with 0.9 molar equivalents of compound B of following formula

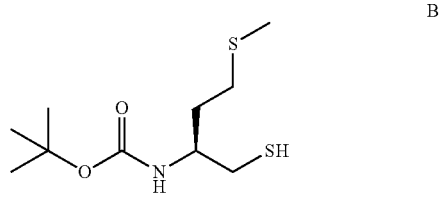
B in solution with 1 molar equivalent of Et$_3$N in same solvent than the one used in step 2a;

(3) preparing compound G of following formula

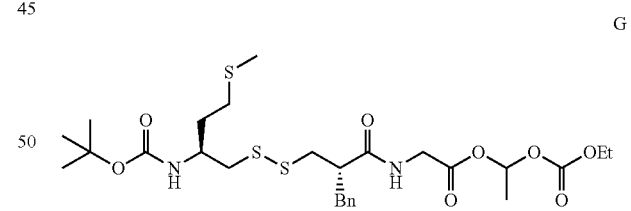
G by
reacting said compound F with amino-ester C of following formula, wherein Y$^-$ is an anion:

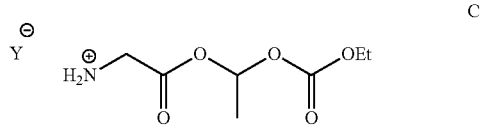
C in polar solvent;
(4) then, recovering salt (I) of followed formula

[Structure of salt I: compound with CO₂H groups (fumarate), H₂N-CH(CH₂CH₂SCH₃)-CH₂-S-S-CH₂-CH(Bn)-C(O)-NH-CH₂-C(O)-O-CH(CH₃)-O-C(O)-OEt]

by
4a) adding 5 molar equivalent of formic acid to said compound G;
4b) exchanging the form ate by a fumarate using a continuous flow technology.

2. The industrial process according to claim 1, wherein crystallization in step 1b comprises the following successive steps:
1b.1) dissolution of quinine salt at solubilizing temperature, then;
1b.2) cooling the mixture obtained in step 1b.1, until temperature ranging from 10° C. to 20° C.;
1b.3) isolating quinine salt obtained after step 1b.2 by filtration.

3. The industrial process, according to claim 1, wherein in step 1a solvent is ethyl acetate.

4. The industrial process according to claim 1, wherein step 1d.1 further comprises the following successive steps:
1d.1.1) suspension of quinine salt obtained in step 1c.3 or 1c.4 in HCl in solution in water, then;
1d.1.2) extraction of compound (D) of following formula

[Structure D: acetyl-S-CH₂-CH(Bn)-COOH]

with an aprotic and polar solvent, in particular with ethyl acetate, then;
1d.1.3) concentration in vacuum to obtain an oil.

5. The industrial process, according to claim 1, further comprising after step 1d.1, the following successive steps:
1d.2.1) alkaline hydrolysis in polar and protic solvent, then
1d.2.2) acidic treatment, then;
1d.2.3) extraction of compound (E) with organic solvent.

6. The industrial process according to claim 1, wherein the recovering of quinine in step 1e comprises the following successive steps:
1e.1) combining the aqueous phases obtained in step 1d.2.1 and in step 1d.2.2, then;
1e.2) adding 20% by weight of aqueous solution of NaOH in water to adjust the pH to 12, then;
1e.3) extracting the resulting mixture obtained in step 1e.2 with AcOEt, then;
1e.4) concentrating under vacuum the resulting organic layer obtained in step 1e.3, then;
1e.5) adding petroleum ether at temperature ranging from 10° C. to 20° C., then;
1e.6) filtrating the resulting solid obtained at the end of step 1e.5 and recovering quinine.

7. The industrial process according to claim 1, further comprising after step 2b and before step 3 the following successive steps:
2b.1) adding water comprising 10% in weight of citric acid to the reaction mixture obtained after step 2b, until pH<7, then;
2b.2) extracting compound F with AcOEt.

8. The industrial process according to claim 7, wherein after step 2b.2 compound F is precipitated in Hexane.

9. The industrial process, according to claim 1, wherein step 3 comprises the following steps:
3a) solubilizing compound F in polar and aprotic solvent, then
3b) to the reaction mixture obtained after step 3a adding 1.2 molar equivalents of O-Benzotriazol-1-yl-N,N,N',N'-tetramethyluronium hexafluorophosphate and diisopropyl-ethyl-amine.
3c) to the reaction mixture obtained after step 3b adding 1.3 molar equivalents of aminoester C.

10. The industrial process according to claim 1, wherein step 3 is performed at a temperature comprised between 2° C. and 10° C.

11. The industrial process according to claim 9, wherein in step 3a, the compound (F) is put in organic solvent at a concentration of 0.05 M-0.3 M.

12. The industrial process according to claim 9, wherein after step 3c compound G is obtained by following successive steps:
3c.1) recovering organic layer containing compound G;
3c.2) precipitating compound G present in organic layer of step 3c.1 by adding a mixture of petroleum ether (hexane)/AcOEt in 8/1-6/1 volume proportion.

13. The industrial process according to claim 12, wherein step 3c.1 comprises the following successive steps:
3c.1.1) adding water to the resulting mixture obtained in step 3c, then;
3c.1.2) without concentrating the reaction solvent, extracting the product obtained after step 3c.1.1 with polar aprotic solvent.

14. The industrial process according claim 1, wherein compound C is prepared by a process comprising the following successive synthetic steps:
α) reacting 1.1 molar equivalents of Boc-glycine with 1.2 molar equivalent of Et₃N in ethyl acetate, then;
β) reacting product obtained in step α with 1 molar equivalents of ethyl-1-chloroethylcarbonate, and 0.2 molar equivalents of potassium iodide.
γ) reacting product obtained in step β with 2 molar equivalents of HCl gas in ethyl acetate at temperature ranging from 5° C. to 10° C., and recovering C.

15. The industrial process according to claim 1, wherein after adding formic acid in step 4a, the process further comprises the following successive steps:
4a.1) co-evaporating product obtained after adding formic acid with toluene giving compound (H), the formate salt of (G), and organic layer with toluene, then;

4a.2) to the compound (H) obtained after step 4a, adding ethyl acetate, and then washing the resulting mixture with brine at a temperature ranging from 0° C. to 10° C.

16. The industrial process, according to claim 1, wherein anion exchange is performed by the following steps:
   4b.1) adding a solution of 2% NaOH by weight in water to a product obtained after step 4a.2 at temperature ranging from 0° C. to 10° C., then;
   4d) adding a solution 5% fumaric acid by weight in EtOH to the mixture obtained after step 4b.1 to isolated crystallized compound (I) using flow continuous process.

17. The industrial process, according to claim 2, wherein the cooling in step 1b.2) is performed at a rate of 3-10° C./h.

18. The industrial process, according to claim 8, wherein after precipitation in Hexane compound F is recrystallized from Hexane/AcOEt, in 5.5/1-7.5/1 in a volume proportion.

19. The industrial process, according to claim 13, wherein in step 3c.1.2) the polar aprotic solvent is AcOEt.

* * * * *